(12) United States Patent
Patterson et al.

(10) Patent No.: US 7,947,441 B2
(45) Date of Patent: May 24, 2011

(54) MOLECULAR DETECTION AND QUANTIFICATION OF ENTEROCOCCI

(75) Inventors: Stacey S. Patterson, Knoxville, TN (US); John H. Paul, St. Petersburg, FL (US)

(73) Assignee: University of South Florida, Tampa, FL (US)

( * ) Notice: Subject to any disclaimer, the term of this patent is extended or adjusted under 35 U.S.C. 154(b) by 455 days.

(21) Appl. No.: 11/735,618

(22) Filed: Apr. 16, 2007

(65) Prior Publication Data

US 2007/0243550 A1   Oct. 18, 2007

Related U.S. Application Data

(60) Provisional application No. 60/744,850, filed on Apr. 14, 2006.

(51) Int. Cl.
C12Q 1/68 (2006.01)
C07H 21/04 (2006.01)

(52) U.S. Cl. .......................................... 435/6; 536/24.33

(58) Field of Classification Search .......................... None
See application file for complete search history.

(56) References Cited

U.S. PATENT DOCUMENTS

| | | | |
|---|---|---|---|
| 4,851,330 A | 7/1989 | Kohne | |
| 5,334,501 A | 8/1994 | Adams et al. | |
| 5,409,818 A | 4/1995 | Davey et al. | |
| 5,650,290 A | 7/1997 | Grant | |
| 5,695,946 A | 12/1997 | Benjamin et al. | |
| 5,723,597 A | 3/1998 | Kohne | |
| 6,001,564 A | 12/1999 | Bergeron et al. | |
| 6,355,421 B1 | 3/2002 | Coull et al. | |
| 6,583,275 B1 | 6/2003 | Doucette-Stamm et al. | |
| 6,821,770 B1 | 11/2004 | Hogan | |
| 7,118,870 B2 | 10/2006 | Field et al. | |
| 7,205,112 B2 | 4/2007 | Paul et al. | |
| 7,422,857 B2 | 9/2008 | Paul | |
| 7,563,577 B2 | 7/2009 | Paul et al. | |
| 7,700,278 B1 | 4/2010 | Paul et al. | |
| 7,888,031 B2 | 2/2011 | Paul | |

OTHER PUBLICATIONS

Bachoon, D.; Gates, K.; King, E. 2005. Rapid Detection of human fecal contamination in estuarine environments by PCR targeting of Bifidobacterium adolescentis. Journal of Microbiological Methods. 68: 76-81.
Baeummer, A.J.; Leonard, B.; McElwee, J.; Montagna, R.A. 2004. A rapid biosensor for viable B. anthracic spores. Anal. Bioanal. Chem. 380: 15-23.
Buckalew, D.W.; Hartman, L.J.; Grimsley, G.A.; Martin, A.E.; Register, K.M. 2006. A long-term study comparing membrane filtration with Colilert defined substrates in detecting fecal coliforms and Escherichia coli in natural waters. Journal of Environmental Management. 80: 191-197.

Fiksdal, L.; Pommepuy, M.; Caprais, M.; Midttun, I. 1994. Monitoring of Fecal Pollution in Coastal Waters by Use of Rapid Enzymatic Techniques. Applied and Environmental Microbiology. 60: 1581-1584.
He, J.; Jiang, S. 2005. Quantification of Enterococci and Human Adenoviruses in Environmental Samples by Real-Time PCR. Applied and Environmental Microbiology. 71: 2250-2255.
Loens, K.; Beck, T.; Goossens, H.; Ursi, D.; Overdijk, M.; Sillekens, P.; Ieven, M. 2006. Development of conventional and real-time NASBA for the detection of Legionella species in respiratory specimens. Journal of Microbiological Methods. 67: 408-415.
Noble, R.T.; Weisberg, S.B.; Leecaster, M.K.; McGee, C.D.; Ritter, K.; Walker, K.O.; Vainik, P.M. 2003. Comparison of Beach Bacterial Water Quality Indicator Measurement Methods. Environmental Monitoring and Assessment. 81: 301-312.
Omar, N. B.; Castro, A.; Abriouel, H.; Lucas, R.; Perez, R.; Martinez-Canamero, M.; Galvez, A. 2004. Quantification of Enterococcus faecalis and Enterococcus faecium in different foods using rRNA-targeted oligonucleotide probes. Journal of Microbiological Methods. 61: 187-192.
Vail, J.H.; Morgan, R.; Merino, C.R.; Gonzales, F.; Miller, R.; Ram, J.L. 2003. Enumeration of Waterborne Escherichia coli with Petrifilm Plates: Comparison and Standard Methods. J. Environ. Qual. 32: 368-373.
Van Der Wolf, J.M.; Van Beckhoven, J.R.C.M.; De Haan, E.G.; Van Den Bovenkamp, G.W.; Leone, G.O. M. 2004. Specific detection of Ralstonia solanacearum 16S rRNA sequences by AmpliDet RNA. European Journal of Plant Pathology. 110: 25-33.
Haugland, R.A.; Siefring, S.C.; Wymer, L.J.; Brenner, K.P.; Dufour, A.P. 2005. Comparison of Enterococcus measurements in freshwater at two recreational beaches by quantitative polymerase chain reaction and membrane filter culture analysis. Water Research. 39: 559-568.
Frahm, E.; Obst, U. 2003. Application of the fluorogenic probe technique (TaqMan PCR) to the detection of Enterococcus spp. and Escherichia coli in water samples. Journal of Microbiological Methods. 52: 123-131.
Behlke et al. 2005. "Fluorescence and Fluorescence Applications." Integrated DNA Technologies. pp. 1-13.
Weusten et al. 2002. "Principles of Quantitation of Viral Loads Using Nucleic Acid Sequence-Based Amplification in Combination with Homogenous Detection Using Molecular Beacons." Nucleic Acids Research. vol. 30. No. 6 e26. pp. 1-7.
Casper, E.T. et al. "A handheld NASBA analyzer for the field detection and quantification of Karena brevis" Harmful Algae, Jan. 2007, 6(1):112-118.
Casper, E.T. et al. "Detection and Quantification of the Red Tide Dinoflagellate Karena brevis by Real-Time Nucleic Acid Sequence-Based Amplification" Applied and Environmental Microbiology, Aug. 2004, 70(8):4727-4732.
Patterson, S.S. et al. "A nucleic acid sequence-based amplification assay for real-time detection of norovirus genogroup II" Journal of Applied Microbiology, Oct. 2006, 101(4):956-963.
Patterson, S.S. et al. "Increased precision of microbial RNA quantification using NASBA with an internal control" Journal of Microbiological Methods, 2005, 60:343-352.
International Search Report dated Nov. 13, 2007 for International Application No. PCT/US2007/009235, 2 pages.
International Preliminary Report on Patentability dated Oct. 14, 2008 for International Application No. PCT/US2007/009235, 4 pages.

Primary Examiner — Robert A Zeman
(74) Attorney, Agent, or Firm — Saliwanchik, Lloyd & Eisenschenk

(57) ABSTRACT

A primer pair and probe for the large subunit ribosomal RNA gene of enterococci for use in a real-time nucleic acid sequence based amplification (NASBA) assay.

1 Claim, 1 Drawing Sheet

The Figure

ENTF1

SEQ ID No 1    5' GATGAGGTGTGGGTAGCGGA 3'

ENTR3

SEQ ID No 2    5'*AATTCTAATACGACTCACTATAGGGAGAA*CTAGTCCAAACAGTGCTCTA3'
SEQ ID No 3    5'*AATTCTAATACGACTCACTATAGGGAGAA*3'

T7 Promoter Region

ENT-PROBE2

SEQ ID No 4    5'FAM-CATGCGAACGAACTTGGAGATAGCTGCGCATG-DABCYL 3'

Stem Structure of Molecular Beacon Molecule         Stem Structure of Molecular Beacon Molecule

SEQUENCE LISTING

<160> NUMBER OF SEQ ID NOS: 4

<210> SEQ ID NO 1
<211> LENGTH: 20
<212> TYPE: DNA
<213> ORGANISM: Enterococcus

<400> SEQUENCE: 1
gatgaggtgt gggtagcgga                                                   20

<210> SEQ ID NO 2
<211> LENGTH: 49
<212> TYPE: DNA
<213> ORGANISM: Enterococcus

<400> SEQUENCE: 2
aattctaata cgactcacta tagggagaac tagtccaaac agtgctcta                   49

<210> SEQ ID NO 3
<211> LENGTH: 29
<212> TYPE: DNA
<213> ORGANISM: Enterococcus

<400> SEQUENCE: 3
aattctaata cgactcacta tagggagaa                                         29

<210> SEQ ID NO 4
<211> LENGTH: 32
<212> TYPE: DNA
<213> ORGANISM: Enterococcus

<400> SEQUENCE: 4
catgcgaacg aacttggaga tagctgcgca tg                                     32

MOLECULAR DETECTION AND QUANTIFICATION OF ENTEROCOCCI

CROSS REFERENCE TO RELATED APPLICATIONS

The present application claims the benefit of U.S. Provisional Patent Application Ser. No. 60/744,850, filed Apr. 14, 2006, the contents of which are herein incorporated by reference.

STATEMENT OF GOVERNMENT INTEREST

This invention was made with Government support under Grant No. 25000 172 00 awarded by the National Science Foundation. The Government has certain rights in the invention.

FIELD OF INVENTION

This invention relates to rapid detection of an organism, specifically, this is a method for detecting and quantifying Enterococci (a human fecal indicator organism) from sea water.

BACKGROUND OF THE INVENTION

The coastal ocean is an important economic and recreational resource that is constantly influenced by human activities. In 2003, there were more than 18,000 days of beach closings throughout the US due to high concentrations of fecal bacteria. This was an increase of more than 51% over the previous year. Health related management of recreational coastal sites is currently undertaken by monitoring fecal coliform and enterococci by membrane filtration. Elevated concentrations of enterococci in marine waters have been shown to have a strong correlation with illness (especially gastrointestinal disease) in exposed individuals therefore making enterococci the indicator organism of choice for saline waters. The problem with this type of standard indicator monitoring is that there is a lag of at least 24-48 hours between when the sample is collected and when the data become available. Changes in the water quality and potential exposures during this delay lead to management decisions and public notifications that are often times inaccurate. To improve our management abilities, a primer pair and probe have been adapted for the large subunit ribosomal RNA gene of enterococci for use in a real-time nucleic acid sequence based amplification (NASBA) assay. This region is highly conserved within all reported species of the *Enterococcus* genus. Using this assay, the equivalent of less than one enterococci colony forming unit (CFU) was detected from a spiked sea water sample (100 ml). Further, there is a negative linear relationship ($R^2=0.9484$) between CFUs obtained by membrane filtration and time to positivity (TTP) readings obtained with the NASBA assay. Therefore, quantitative estimates of enterococci are possible over at least four orders of magnitude and all positive samples amplified within forty-three minutes. By coupling this real-time NASBA assay to the inventors' existing field RNA extraction procedure and portable NASBA detection device, this technology will provide a simple, rapid (<1 hr), convenient testing format for coastal sites and greatly improve the health risk assessment of these regions.

Unlike polymerase chain reaction (PCR) based methods, NASBA is able to amplify RNA in a DNA background, and thus, only viable targets will be detected. This is important for indicator monitoring because only recent pollution events will be detected and false positive amplifications of naked DNA present in the sample will be eliminated. Indicator bacteria are chosen because of their ability to survive longer than the pathogenic organisms in question and therefore only viable bacteria should be considered as part of a risk analysis.

SUMMARY OF INVENTION

This is a method for the detection and quantification of Enterococci. Enterococci is the USEPA approved indicator organism used to monitor for fecal pollution in saline waters. Current methods rely on membrane filtration and even though the direct enumeration of these microorganisms using membrane filtration and plating has been available for years, there continue to be outbreaks associated with fecal contamination. The problem is that there is a lag of at least 24-48 hours between when the sample is collected and when the data become available. Changes in the water quality and potential exposures during this delay lead to management decisions and public notifications that are often times moot. To improve management abilities, there is a need for rapid detection and quantification of appropriate bacterial indicators in coastal waters and sediments to ensure the safety of these resources for their multiple users. The present NASBA based method addresses this issue by quantitatively amplifying the target RNA and providing results in less than one hour.

BRIEF DESCRIPTION OF THE DRAWINGS

For a fuller understanding of the invention, reference should be made to the following detailed description, taken in connection with the accompanying drawings, in which:

The FIGURE shows sequences for primers and probe for NASBA amplification of Enterococci.

DETAILED DESCRIPTION OF THE PREFERRED EMBODIMENT

NASBA primers and probes were designed based on homologous regions of the large subunit ribosomal RNA gene (The FIGURE). This region is highly conserved within all reported species of the *Enterococcus* genus (Haugland et al., 2005). Previous researchers (Frahm and Obst, 2003) used this region as the priming site for the development of a Taqman PCR assay for enterococci detection. The primers have been modified to best fit the NASBA amplification requirements and molecular beacon design criteria as well as minimize the cross hybridization to each other. This primer set has been tested against *Enterococcus faecalis* and *E. faecium*, and *E. avium*, as well as several other genera of Gram positive and Gram negative bacteria to determine the specificity of the assay and ensure that no cross reactivity occurs to non-target organisms. Data thus far indicate that the primer set is specific to the genus enterococci.

The assay sensitivity has been evaluated using serially diluted RNA isolated from enterococci cells. It is also possible to include cell extract samples from individual species as well as mixtures of all of the enterococci species available. Because ribosomal RNA tends to have a complex secondary structure, the NASBA assay was initiated by a 65° C. denaturing step for 3 minutes prior to the 41° C. amplification step (60 to 90 minutes). This initial denaturation is required for some, but not all NASBA assays and its requirement for efficient amplification of enterococci still needs to be evaluated.

Amplification inhibitors are often co-purified with natural environmental samples. These inhibitors have been encountered in coastal water filtrates (Casper et al., 2005b). However, this inhibition tends to occur in sample volumes greater than 200 ml. For enterococci samples, the sample volume will always be less than 100 ml (as used by the DOH). Also, an internal control (IC-NASBA protocol) is included that will be used to normalize the amplification results (Patterson et al., 2005). This approach will increase the precision of quantification, and reduce the amount of false negative results. Because the internal control molecule contains the same priming site as the target, the amplification reaction becomes competitive. Serial titrations of internal control RNA determine the optimal concentration to allow for consistent quantification of enterococci within the expected environmental concentrations (Patterson et al, 2005).

REFERENCES

The following citations are incorporated herein by reference:

Haugland R A, Siefring S C, Wymer L J, Brenner K P, Dufour A P. 2005. Comparison of *Enterococcus* measurements in freshwater at two recreational beaches by quantitative polymerase chain reaction and membrane filter culture analysis. Water Res. 39(4):559-68.

Frahm E, Obst U. 2003. Application of the fluorogenic probe technique (TaqMan PCR) to the detection of *Enterococcus* spp. And *Escherichia coli* in water samples. J Microb Meth 52: 123-131.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method for quantifying Enterococci in a sample of saline water, said method comprising:

lysing at least one test microbe in the sample;
extracting a sample nucleic acid from the at least one microbe;

performing nucleic acid sequence based amplification, wherein said amplifying step comprises contacting said sample nucleic acid with a pair of primers to produce an amplification product, wherein said pair of primers comprises a first primer and a second primer, wherein said first primer comprises SEQ ID NO:1, and said second primer comprises SEQ ID NO: 2; and quantifying the amplification product, wherein the amount of amplification product is indicative of the amount of Enterococci in a sample of saline water.

* * * * *